United States Patent
Hopkins

(10) Patent No.: US 9,682,173 B2
(45) Date of Patent: Jun. 20, 2017

(54) SOLUTIONS FOR TISSUE ENGINEERING AND METHODS OF USE

(75) Inventor: Richard Hopkins, Kansas City, MO (US)

(73) Assignee: The Children's Mercy Hospital, Kansas City, MO (US)

( * ) Notice: Subject to any disclaimer, the term of this patent is extended or adjusted under 35 U.S.C. 154(b) by 232 days.

(21) Appl. No.: 12/483,196

(22) Filed: Jun. 11, 2009

(65) Prior Publication Data

US 2010/0035344 A1    Feb. 11, 2010

Related U.S. Application Data

(60) Provisional application No. 61/060,790, filed on Jun. 11, 2008, provisional application No. 61/060,796, filed on Jun. 11, 2008.

(51) Int. Cl.
*A61L 27/36* (2006.01)
*C12N 5/00* (2006.01)

(52) U.S. Cl.
CPC ....... *A61L 27/3695* (2013.01); *A61L 27/3604* (2013.01); *C12N 5/0068* (2013.01); *A61L 2430/40* (2013.01); *C12N 2521/00* (2013.01); *C12N 2533/90* (2013.01)

(58) Field of Classification Search
CPC ............. A61L 2430/40; A61L 27/3695; C12N 5/0068; A61K 27/3604
See application file for complete search history.

(56) References Cited

U.S. PATENT DOCUMENTS

| | | | |
|---|---|---|---|
| 6,242,573 B1 * | 6/2001 | Goto et al. | 530/356 |
| 6,479,064 B1 * | 11/2002 | Atala | 424/423 |
| 2004/0265268 A1 * | 12/2004 | Jain | 424/85.1 |
| 2005/0265980 A1 * | 12/2005 | Chen | C12N 5/0647 424/93.7 |
| 2006/0154367 A1 * | 7/2006 | Kihm et al. | 435/366 |
| 2006/0210960 A1 * | 9/2006 | Livesey et al. | 435/2 |
| 2007/0020248 A1 * | 1/2007 | Everaerts et al. | 424/93.21 |
| 2007/0141100 A1 * | 6/2007 | Sung et al. | 424/423 |
| 2007/0197890 A1 * | 8/2007 | Boock et al. | 600/365 |
| 2007/0254005 A1 * | 11/2007 | Pathak et al. | 424/423 |
| 2007/0276037 A1 * | 11/2007 | Woo | 514/546 |
| 2007/0276507 A1 * | 11/2007 | Bertram et al. | 623/23.65 |
| 2008/0004713 A1 * | 1/2008 | Nakamura et al. | 623/23.72 |
| 2008/0095757 A1 * | 4/2008 | Levin | 424/94.63 |
| 2010/0015710 A1 * | 1/2010 | Jung et al. | 435/377 |

FOREIGN PATENT DOCUMENTS

WO    WO2006026325    *   3/2006

OTHER PUBLICATIONS

Raeder et al Invest Ophthalmol Vis Sci. 2007; 48:5484-5493.*
Andega et al (Journal of Controlled Release 77 (2001) 17-25.*

* cited by examiner

*Primary Examiner* — Anoop Singh
(74) *Attorney, Agent, or Firm* — Tracey S. Truitt; Armstrong Teasdale LLP

(57) ABSTRACT

The present invention provides for solutions and methods of preparing a decellularized tissue for recellularization. The solutions provide collagen conditioning to restore collagen triple helix structure, strengthening of the collagen structure of the tissue, and biologically preparing the decellularized tissue by placing it in an environment that promotes recellularization. Methods and solutions for recellularization of a decellularized tissue, in accordance with the present invention, are also provided.

5 Claims, No Drawings

SOLUTIONS FOR TISSUE ENGINEERING AND METHODS OF USE

RELATED APPLICATIONS

This application relates to and claims priority to U.S. Provisional Patent Application No. 61/060,790, which was filed Jun. 11, 2008 and to U.S. Provisional Patent Application No. 61/060,796, which was filed Jun. 11, 2008, both of which are incorporated herein by reference in their entireties. All applications are commonly owned.

BACKGROUND

Tissue engineering is a very complicated and highly technical field. One of the possible methods for tissue engineering involves the growth of new tissue using a framework or scaffold from tissues harvested from an animal or human. In such methods, the harvested tissue is first treated to remove all cell debris and other material. This process prepares the tissue for reseeding with fresh cells to promote new cell growth and proliferation. However, the process of removing all cell debris has the effect of placing stress on the harvested tissue, usually resulting in the loss of collagen alignment and collagen structure. The potential for varying degrees of collagen fraying and alterations of collagen fiber tertiary structure and polarity of the collagen triple helix exists after this decellularization process. Collagen that has not been irreversibly cross-linked is degraded by MMPs and re-enters the protein synthesis pathway via its constituent amino acids. The loss of collagen structure leads to voids in the structure of the tissue wall and destabilization of the harvested tissue. Additionally, typical enzyme, detergent and solvent treatments used for decellularization result in significant loss of extracellular matrix (ECM) proteins and ECM soluble molecules such as proteoglycans and glycosaminoglycan's (GAGs). There is significant moisture loss and the protective envelope of proteoglycans and GAG's that surround the structural proteins are significantly depleted.

Promoting and accelerating cell growth once the tissue is reseeded is also a difficult process. In order to promote growth of synthetic tissue and cell growth, the harvested tissue, acting as the frame or scaffold, requires a very specific environment. This process can be further complicated by any allergies or rejection responses a patient might experience when the engineered tissue is introduced into the recipient.

Accordingly, what is needed are preparations which rebuild the tertiary structure of collagen to provide a strong framework or scaffolding to support the growth of new cells. What is further needed is an environment that restores or prevents further loss of moisture, ECM proteins, ECM soluble molecules, lubricant characteristics, and emollient characteristics of an engineered or decellularized tissue. What is still further needed is an environment that promotes and supports the growth of cells seeded into decellularized harvested tissue to create engineered tissues.

SUMMARY OF THE INVENTION

The present invention overcomes the problems inherent in the prior art and provides a distinct advantage in the state of the art by providing solutions and methods of using such solutions in tissue engineering applications. The solutions and methods disclosed are used to protect and prepare tissue for tissue engineering applications in addition to promoting growth of engineered tissue. The tissue engineered constructs resulting from this treatment are more successful when implanted and produce less calcium deposits than previous implanted tissue.

In a preferred embodiment, the method is comprised of a two-step pretreatment regimen including a collagen conditioning step and a biological preparation step. Preferably, the biological preparation step comprises protein insudation. In an alternate embodiment, the pretreatment regimen additionally comprises a third step, a structural strengthening step. Preferably, this step is carried out after the collagen conditioning step, but before the biological preparation step.

Preferably, the first step promotes collagen conditioning. This step includes the use of two solutions. The initial solution (Solution 5) is designed to wash out any residual storage solution and then to "condition" the collagen so as to protect and restore fiber alignment and moisture, and to fill and expand the space in the tissue originally occupied by soluble ECM proteins. Solution 5 generally comprises saline and a sugar alcohol. Preferably the saline is normal saline, and even more preferably is comprised of about 5-25 gm/NaCl/SL 0.9% physiologic saline, more preferably about 20 gm/NaCl/SL physiologic saline, more preferably about 10-20 gm/NaCl/SL 0.9% physiologic saline, and most preferably about 18 gm/NaCl/SL 0.9% physiologic saline. In a preferred embodiment, the sugar alcohol is selected from the group consisting of glycol, glycerol, erythritol, arabitol, Xylitol, Ribitol, Mannitol, Sorbitol, Isomalt, Maltitol, and Lactitol. In a most preferred embodiment, the sugar alcohol is Mannitol, and even more preferably is in the solution at a concentration of about 12.5 to 100 gm Mannitol/2 L, more preferably about 17.5 to 80 gm Mannitol/2 L, more preferably about 22.5 to 60 gm Mannitol/2 L, even more preferably about 24 to 40 gm Mannitol/2 L, even more preferably about 24.5 to 27.5 gm Mannitol/2 L, and most preferably about 25 gm Mannitol/2 L.

The next solution used in the collagen conditioning step ("Solution 2") has the effect of conditioning collagen present in the tissue by strengthening the collagen bonds and helping the collagen reform its natural Madras helix and collagen to collagen fibril alignment. Advantageously, such conditioning results in a better matrix for synthetic cellular growth. Solution 2 generally comprises, solvent alcohols, fatty alcohols, lubricants, and ECM protein restoration agents.

The solvent alcohol(s) can be any conventional solvent alcohol(s), but is preferably ethyl alcohol. Preferably, the amount of the solvent alcohol used is from about 10% to 70%, more preferably between 20% and 60%, still more preferably between 30% and 50%, even more preferably between 35% to 45%, and most preferably about 40%. In an embodiment where ethyl alcohol is used, it is preferably used in an amount of about 10% to 70%, more preferably between 20% and 60%, still more preferably between 30% and 50%, even more preferably between 35% to 45%, and most preferably about 40%.

Similarly, the fatty alcohol(s) can be any conventional fatty alcohol(s), and is preferably one that has emollient, surfactant, lubricant and emulsifier properties. Preferably, the fatty alcohol is present in an amount from about 0.01 to 1.00M, more preferably from about 0.02 to 0.85M, even more preferably from about 0.03 to 0.75M, more preferably from about 0.04 to 0.65M, more preferably from about 0.05 to 0.50M, and most preferably about 0.1M for each alcohol present. In a particularly preferred embodiment, the fatty alcohol is selected from the group consisting of cetyl alcohol, myristyl alcohol, lauryl alcohol, and combinations thereof. In an additionally preferred embodiment cetyl, myristyl and lauryl alcohol are all used. In yet another preferred embodiment, only myristyl and lauryl alcohol are used.

In an alternative embodiment, a surfactant and/or lubricant is included and will be selectable by those of skill in the art. A surfactant, for purposes of the present of the present invention, is an agent that has one or more the following properties: emulsifiers, detergents, foam inhibitors, wetting agents, lubricants, and humectants. Preferred surfactants and will be capable of targeted modulation of specific proteoglycans via exogenous addition, endogenous stimulation with growth factors, or mechanical stimulation, which all contribute to native tissue properties in engineered tissues. Preferred surfactants are selected from the group consisting of glycerin, propylene glycol, glycerol triacetate, sorbitol, xylitol, malitol, polydextrose, lactic acid, Tween 20, and combinations thereof. Preferably, the surfactant is Tween 20, which also acts as a humectant. Preferably, when Tween 20 is used, it is present in an amount of about 0.005% to 1% by volume, more preferably from about 0.006% to about 0.5% by volume, even more preferably about 0.007% to 0.1% by volume, and, even more preferably from about 0.008% to 0.05% by volume, and most preferably it is present in an amount of about 0.01% by volume. In an alternate embodiment, the surfactant is glycerin. In other preferred embodiments, the surfactant is a tenside, more preferably the surfactant is selected from the group consisting of ionic compounds, cationic compounds, zwitterionic compounds, and nonionic compounds. When the surfactant is a nonionic compound, it is preferably selected from the group consisting of nonionic surfactants of the fatty alcohol group, cocamides, poloxamers, alkyl polyglucoside, and combinations thereof. Of these, nonionic surfactants of the fatty alcohol group are particularly preferred. In a preferred embodiment the surfactant has the properties of a lubricant and is selected from the group consisting of oils, non-sulfated GAGs, fibronectin, chondroiton $SO_4$, heparin $SO_4$, keraton $SO_4$, proteoglycans, decorin, serglycin, syndeum, aggrecon, heparin, and combinations thereof.

In a most preferred embodiment, the surfactant has the properties of a lubricant is hyaluronan. Hyaluronan is a polymer that has different chemical properties depending on molecular weight. Preferably, hyaluronan is a mixture of low, medium, and high molecular weight carbohydrate polymers. In a most preferred embodiment, hyaluronan is purified from the umbilical cord, having an average molecular weight of about 3,140,000 daltons. The concentration of hyaluronan is preferably from about 30 to 300 µg/L, more preferably from about 40 to 250 µg/L, more preferably from about 50 to 200 µL, even more preferably from about 60 to 150 µg/L, still more preferably from about 70 to 100 µg/L, and most preferably about 80 µg/L. In preferred forms, a potassium salt hyaluronan composition is used. Sources of hyaluronan that have greater percentage of low molecular weight polymer fragments are avoided because they can be pro-inflammatory. Sources of hyaluronan with higher molecular weight tend to increase viscosity.

In yet another alternate embodiment, Solution 2 further comprises an emollient. Preferably the emollient is selected from the group consisting of glycerin, diprobase, and combinations thereof. In a preferred embodiment, the emollient is present in an amount from about 0.005% to 1% by volume. Preferably, when glycerin is used, it is preferably present in an amount of about 0.005% to 1% by volume, more preferably from about 0.006% to about 0.5% by volume, even more preferably about 0.007% to 0.1% by volume, and, even more preferably from about 0.008% to 0.05% by volume, and most preferably it is present in an amount of about 0.01% by volume.

The ECM protein restoration agent is preferably a biocompatible ECM component. In preferred forms, the ECM protein restoration agent is selected from the group consisting of aggrecans, versicans, decorins, biglycans, fibromodulins, laminins, proteoglycans, albumin, salt poor albumin, serum from the intended recipient of the engineered tissue, endogenous plasma proteins, fibronectins, lipoproteins, polysaccharides, immunoglobulins, dissacharides, signaling proteins, any extracellular matrix components, immunoglobulins, disaccharides, signaling proteins, any typical mammalian extracellular matrix protein, and combinations thereof. In particularly preferred forms, the agent is selected from the group consisting of proteoglycans, aggrecans, versicans, decorins, biglycans, fibromodulins, laminins, and combinations thereof. Of these, proteoglycans such as hyaluronan, heparin $SO_4$, chondroitan sulfate, and especially hyaluronan, are most preferred.

In particularly preferred forms of the present invention, Solution 2 comprises ethyl alcohol, lauryl alcohol, myristyl alcohol, heparin, hyaluronan, and normal saline. In an additionally preferred embodiment, citric acid is included in Solution 2. Preferably, the citric acid has anti-calcification properties, is a mild cross-linker, and has pH restoration properties to optimize the collagen-helix interactions. In embodiments where citric acid is used, it is preferably used in an amount from about 0.5 to 10 g/L, even more preferably from about 0.7 to 9.5 g/L, even more preferably from about 1.0 to 9 g/L, even more preferably from about 2.5 g/L to about 8 g/L, and most preferably about 7.7 g/L.

The method for the collagen conditioning step generally involves the steps of removing all storage solution from the harvested tissue, rinsing the tissue, and transferring into a sterile flask, using sterile techniques. Once the tissue is in the flask, Solution 5 is added and the solution is allowed to decant on a rocker plate at about 25 RPM for about an hour. Solution 2 is then added to the tissue and allowed to decant on a rocker plate at about 30 RPM for about 30 minutes. This step includes the use of a number of fatty alcohols to restore the collagen triple helix conformation and collagen-to-collagen fibril alignment. The heparin and hyaluronan restore molecular polarity of the collagen triple helix and reestablishes a moisture envelope around the collagen and elastin fibers that is similar to the normal functionality of proteoglycans and GAG's. Differential scanning calorimetry has demonstrated marked effects by many detergents on the structural protein, moisture content and ECM interactions. Preferred processing agents do not destabilize the collagen helical structure. Processing agents are preferably selected from the group consisting of ionic detergents, cationic detergents, zwitterionic detergents, nonionic detergents, water, osmotic agents, mannitol, dextran, RNAse, DNAse, sugars, alcohols, and combinations thereof. Overall, this step conditions collagen to reform the triple helix structure stabilizing the tissue and allowing it to recover from preparatory procedures, such as decell.

For a three-step pretreatment regimen, the structural strengthening step is preferably carried out after the collagen conditioning step and comprises the use of solutions for collagen structural strengthening. The method for structural strengthening involves the use of two solutions described herein. The first collagen structural strengthening solution ("Solution 3") comprises a collagen or elastin cross-linking agent and $H_2O$. The $H_2O$ is preferably present in an amount of about 25% to 75% of the volume of the container, more preferably, about 50% of the volume of the container. In a preferred embodiment the collagen or elastin cross-linking agent is selected from the group consisting of water-soluble cross-linking agents, glutaraldehyde type agents, photoactivated dyes, carbodiimides, diaminohexane, chromium, vegetable tannins, non-enzymatic glycosylation agents, steroid-like compounds, and combinations thereof. Any cross-linking agent can be used. Preferably, the cross-linking agent is citric acid. In embodiments where citric acid is used, it is preferably used in an amount from about 0.5 to 10 g/L, even more preferably from about 0.7 to 9.5 g/L, even more preferably from about 1.0 to 9 g/L, even more preferably from about 2.5 g/L to about 8 g/L, and most preferably about 7.7 g/L. Preferably, citric acid has a molecular weight of about 192.14 g/Mol. Preferably, about 0.01 to 0.50 M (molar) is used, even more preferably about 0.02 to 0.40M, even more preferably about 0.03 to 0.3M, and most preferably about 0.04M. In the concentration and amount, as used in the present invention, citric acid is a mild collagen and/or elastin cross-linking agent. In an alternate preferred embodiment, the collagen cross-linking agent is a steroid-like compound, and even more preferably, the cross-linking agent is ginsenoside Rg1. In an embodiment where ginsenoside Rg1 is used, it is preferably present in an amount from about 10 ngms/ml to about 100 ngms/ml, preferably about 50 ngms/ml. In an additional alternate embodiment, both citric acid and ginsenoside Rg1 can be used. Solution 3 has the effect of aiding in the cross-linking of collagen providing strength to the harvested tissue as well as avoiding altering the molecular bonding milieu.

The second collagen structural strengthening solution ("Solution 4") comprises normal saline and an anti-mineralization agent. While any anti-mineralization agent will work, in a preferred embodiment the anti-mineralization agent is selected from the group consisting of alpha-amino oleic acid, ethanol, and citric acid. In a particularly preferred embodiment, the anti-mineralization agent is citric acid. In embodiments where citric acid is used, it is preferably used in an amount from about 0.5 to 10 g/L, even more preferably from about 0.7 to 9.5 g/L, even more preferably from about 1.0 to 9 g/L, even more preferably from about 2.5 g/L to about 8 g/L, and most preferably about 7.7 g/L. Preferably, citric acid has a molecular weight of about 192.14 g/Mol. Preferably, about 0.01 to 0.50 M (molar) is used, even more preferably about 0.02 to 0.40M, even more preferably about 0.03 to 0.3M, and most preferably about 0.04M. In an alternate embodiment, ethanol is used as an anti-mineralization agent. Solution 4 acts as a demineralizer and an anti-calcification agent which accelerates collagen production.

The structural strengthening step involves removing the post decell storage solution the tissue had previously been placed in, as described in Example 1, rinsing with normal saline, and placing tissue in Solution 3. The tissue is then allowed to rock on a rocker plate at pH 7.4, temperature 21° C. for 2 hours. The tissue is rinsed again and then placed in Solution 4 on a rocker plate for 15 minutes at 30 RPM. The process of placing tissue in solution 3, rinsing, and then placed in solution 4 provides collagen cross-linking which strengthens the collagen bonding and protein present in the tissue. The citric acid in Solution 4 acts as an anti-calcification agent.

The final step of the biological preparation step prepares tissue for recellularization. This step is either carried out after the collagen conditioning step, using a two-step treatment or after the structural strengthening step using a three-step treatment. This step utilizes a pre-op seeding solution. This solution ("Solution 1") provides a biological milieu that accelerates synthetic growth while lessening the severity of side affects associated with allergies to any of the components of synthetic cell growth. Solution 1 generally comprises at least 7 components of a group selected from the group consisting of traditional cell culture media, serum, insulin, growth promoters, myofibroblast phenotype maintenance agents, L-glutamine, buffer, heparin, steroid-like compounds, chondroitin sulfate, ethyl pyruvate, ascorbic acid, ascorbate, a collagen or elastin cross-linking agent, a co-enzyme, signaling proteins or compounds, and antibiotic agents. Preferred growth promoters include, but are not limited to, heparin, IGF, TGF-$\beta$1, chondroitin sulfate, insulin, and combinations thereof. Growth promoters such as PDGF and HGF are not preferred for purposes of the present invention. Preferred myofibroblast phenotype maintenance agents include, but are not limited to TGF-$\beta$1, chondroitin sulfate, ascorbic acid, ascorbate, and combinations thereof. In an alternate embodiment, Solution 1 further comprises agents which are intermediate metabolize supporters. Preferably, these intermediate metabolize supporters are selected from, but not limited to, co-enzyme Q10, L-glutamine, ethyl pyruvate, spingoside phosphate, and combinations thereof.

When insulin is used, it is preferably present in an amount from about 1 units/ml to about 10 units/ml, more preferably from about 1.5 units/ml to about 5 units/ml, and, most preferably, it is present in an amount of about 2 units/ml.

In one embodiment, Solution 1 additionally comprises Ginsenoside Rg1. In an alternate embodiment, the solution does not comprise Ginsenoside Rg1, but alternately comprises citric acid. Preferably, the citric acid has anti-calcification properties. Preferably, if Gensenoside Rg1 is present, Solution 1 contains about 1-20 ngm/ml, preferably, about 15 ngm/ml, more preferably, about 5-15 ngm/ml, more preferably about 5 ngm/ml, even more preferably, about 7-12 ngm/ml, and most preferably, about 10 ngm/ml of Gensenoside Rg1. If citric acid is present, Solution 1 contains about 0.5-5 gm, preferably, about 3 gm, more preferably, about 1-4 gm, preferably, about 2.5 gm, even more preferably, about 1.5-2 gms, preferably about 1.54 gm of citric acid.

While any traditional cell culture media will work, in a preferred embodiment media is selected from the group consisting of DMEM+F12, MEM, Hank's solution, JCI99, and RPMI 1600. In a most preferred embodiment, the media is DMEM+F12

Serum is preferably selected from serum specific to the donor species, serum specific to the recipient species, anaglous serum from putative recipient, and combinations thereof. In an embodiment comprising serum, serum is present in a ration of volume from about 1:5 to 4:5, with the most preferred ratio being about 2:5 by volume.

Myofibroblast phenotype maintenance agents are preferably selected from the group consisting of TGF-$\beta$1, TGF-$\beta$2, TGF-$\beta$3, bFGF, FGF2, sphingosine, sphingosine-1-phosphate and combinations thereof. The myofibroblast phenotype maintenance agent, preferably TGF-$\beta$1, when present, is preferably present in an amount from about 0.1 ngm/ml to about 20.0 nmg/ml and more preferably about 10 nmg/ml.

The buffer, when used, is preferably selected from the group consisting of Zwitterionic Buffers, EDTA-Tris, trimentylglycine, glycine, BES, MES, with Hepes buffer being particularly preferred. Preferably, buffer is used in an amount from about 5 to 20 mM/L, even more preferably from about 7 to 19 mM/L, more preferably from about 9 to 17 mM/L, still more preferably from about 12 to 16 mM/L, and most preferably about 15 mM/L.

Preferred collagen or elastin cross-linking agents are selected from the group consisting of water-soluble cross-linking agents, glutaraldehyde type agents, photoactivated dyes, carbodiimides, diaminohexane, chromium, vegetable tannins, non-enzymatic glycosylation agents, and combinations thereof.

Preferred antibiotic agents are selected from the group consisting of amphoterian-B, vancomycin, gentamicin, and combinations thereof. Preferably, the antibiotics are present in an amount of about 10 ugm/ml to about 1000 ugm/ml. When amphoterian-B is used, it is preferably used in an amount of about 5 to 50 ngm/ml, more preferably about 10 to 30 ngm/ml, and most preferably about 25 ngm/ml. When vancomycin is used, it is preferably used in an amount of about 25 to 100 ngm/ml, more preferably about 30 ngm/ml to about 60 ngm/ml, and most preferably, about 50 ngm/ml is used. When gentamicin is used, it is preferably used in an amount of about 100 to 1000 ngm/ml, more preferably, from about 250 to 750 ngm/ml, and most preferably, 500 ngm/ml is used.

In an alternate embodiment of the biological preparation step, a protein insudation is carried out. Preferably, the protein insudation solution comprises plasma and one or more antibiotics. In a preferred embodiment, the plasma is species specific, and, more preferably, the plasma is from the recipient. The antibiotics are preferably amphotericin, vancomycin, gentamicin, and combinations thereof. The preferred amounts of the antibiotics are the same as in the embodiment above. Preferably, all three antibiotics are present. The solution may also be augmented with plasma. Plasma is preferably used in an amount from about 5% to 100% of the volume of the container in which the solution is being held, even more preferably about 10% to 80%, even more preferably about 12% to 70%, more preferably from about 15% to 60%, still more preferably from about 18% to 50%, and most preferably about 20%. Preferably the augmented plasma is 5% Plasma-Lyte, fresh or frozen species specific plasma, or recipient plasma. The method of the protein insudation comprises treatment of the tissue with heparin, followed by placement of the tissue in the protein insudation solution. Preferably, the protein insudation solution is augmented with species specific plasma and, even more preferably, with recipient plasma.

Another embodiment of the present invention involves reseeding of a decellularized tissue. In a preferred embodiment, the decellularized tissue is a heart valve. Preferably, the recellularization incorporates Solution 1. The method of recellularization comprises at least two phases: a Seeding Phase, and a Cell Differentiation and Migration Phase. In a preferred embodiment, the method of recellularization additionally comprises a cell proliferation step. In this preferred embodiment, the cell proliferation step is carried out prior to the seeding and cell differentiation phases.

In the Cell Proliferation Phase, a patient, preferably a recipient for the valve transplant, is given Ancef, preferably about 1 gm, about 1 hour before the bone marrow is harvested. Bone marrow is then harvested from the heart valve recipient. A decellularized tissue, preferably conditioned according to the methods of the present invention, was set aside for later use. A separate incubator, preferably a bioreactor, was set up and the recipient bone marrow was added. The bioreactor is preferably set up for a hypoxic environment. Preferably the oxygen content is about 3% to 19%, more preferably about 4% to about 17%, even more preferably about 5% to 15%, still more preferably about 6% to about 10%, and most preferably about 7%. The temperature in the bioreactor is preferably about 37° C. In a preferred embodiment, the incubator is coated with a non-adherent surface, preferably agarose, so that the bone marrow cells do not adhere to the wall of the incubator creating spheroid bodies of mesenchymal stromal cells. Preferably, the incubator mesenchymal stem cell proliferating media, preferably MGCSM (Lonza Group Ltd, Switzerland), and related nutrients are added. Preferably the nutrients are MCGM (Lonza Group Ltd, Switzerland). The bone marrow and media are preferably allowed to incubate for 48-96 hours. The Cell Proliferation Phase allows the proliferation and amplification of bone marrow cells while preventing differentiation of those cells. Additionally, the bone marrow cells are prevented from adhering to the surface of the bioreactor.

In the next phase, the Seeding Phase, a decellularized tissue is placed with MGCSM and MCGM and bone marrow cells in a bioreactor. In a preferred embodiment, the Cell Proliferation Phase precedes the Seeding Phase, and the decellularized tissue is added to the incubator with fresh MGCSM and MCGM (nutrient pellet to supplement the MGCSM media). Preferably, the Seeding Phase, allows the mesenchymal component of the bone marrow to migrate into the scaffold of the decellularized tissue and adhere, thus seeding the tissue. In a preferred embodiment, the bioreactor used in this phase is coated with a non-adherent surface, preferably agarose, such that the bone marrow cells migrate into the decellularized tissue while continuing to proliferate. Preferably, the incubator at this stage is calibrated to provide a hypoxic environment. In an embodiment where the Cell Proliferation Phase precedes the Seeding Phase, this hypoxic environment is maintained. This hypoxic environment helps prevent bone marrow differentiation. The decellularized tissue is preferably allowed to incubate for 4-7 days. In a preferred embodiment, the pH of the solution and/or media in the bioreactor is about 6.2 to 7.2, more preferably about 6.4 to 7.1, even more preferably about 6.5 to 7.0, and most preferably about 6.8. A falling pH is an indicator that the cells are proliferating, however, preferably the pH is kept above 6.2. During this phase the mesenchymal stem cells adhere to the valve.

In the third phase, or the Cell Differentiation and Migration Phase, the MSCGM media is discarded and replaced with Solution 1 in the bioreactor containing the heart valve and bone marrow. Preferably, a separate bioreactor is used for this phase which has the capability to provide cyclic pressure and flow. Preferably, prior to the addition of Solution 1, the oxygen environment is altered to create a hyperoxic environment. The hyperoxic environment preferably has an oxygen content from about 22% to 70% oxygen, even more preferably about 25% to 65%, even more preferably about 30% to 60%, even more preferably about 35% to 58%, still more preferably about 40% to 55%, and most preferably, about 50%. Preferably, the Cell Differentiation and Migration phase allows the mesenchymal stem cells to begin to differentiate and migrate further into the scaffold of the decellularized tissue. Preferably, the bone marrow cells are conditioned to become mesenchymal stem cells, adult stem cells, or multipotent cells. Preferably, the mesenchymal stem cells differentiate into cells specific to the decellularized tissue. In a preferred embodiment, where a heart valve is utilized, the mesenchymal stem cells differentiate into valve interstitial and valve endothelial cells. The Cell Differentiation and Migration Phase allows for differentiation, proliferation, and migration of the differentiated cells, thus, repopulating the decellularized tissue. Preferably, a mechanical environment is introduced into the bioreactor such that cyclic pressure and cyclic flow occurs. In a preferred embodiment, the cyclic pressure rates for the bioreactor begin at 3 mmHg/0 (10-20 beats per minute) and are ramped up gradually each day to a final cyclic pressure of 25 mmHg/10 (20-100 beats per minute). Preferably, the cyclic pressure can go up to 750 mmHg, but is preferred at a rate of 3 mmHg to 200 mmHg, more preferably about 5 mmHg to about 100 mmHg, and most preferably about 25 mmHg. In a most preferred embodiment, the cyclic pressure is gradually increased over the course of the time the decellularized tissue is in the bioreactor. In an embodiment where a heart valve is used, this phase conditions the valve to the flow in the heart so that it has a better chance of success once implanted. Half of Solution 1 is preferably replaced when the pH of the bioreactor environment falls to less than 6.4. This process is preferably repeated over the course of 2-6 days, but more preferably over the course of about 3 to 5 days.

In a preferred embodiment, the cyclic pressure is kept at low levels while the heart valve is conditioned. In an embodiment where a heart valve is utilized, this low cyclic pressure allows the leaflets of the heart valve to be loaded with mesenchymal stem cells when then differentiate into valve interstitial and valve endothelial cells. The cells travel further onto the scaffold of the leaflet and into the matrix of the leaflet tissue. This leads to a heart valve that more closely resembles a normal heart valve.

In an additionally preferred embodiment, the now seeded tissue is allowed to incubate in heparinized recipient blood for 5 to 25 minutes, while the tissue is waiting to be transplanted into the patient. Heparinized recipient blood includes the addition of heparin to blood from the patient receiving the tissue.

Thus, one aspect of the invention provides a method of preparing a decellularized tissue for recellularization comprising the steps of conditioning the collagen in the decellularized tissue and biologically preparing the decellularized tissue by placing the decellularized tissue in an environment that promotes the recellularization of the tissue. Generally, the collagen conditioning step includes the steps of strengthening the collagen, aligning the collagen, and decreasing the fraying of said collagen. In some preferred forms, the collagen conditioning step comprises the steps of contacting the tissue with a solution comprising saline and a sugar; and contacting the tissue with a solution comprising one or more alcohols, lubricants, and ECM proteins. Preferably the saline is normal saline and more preferably is NaCl/SL 0.9% physiologic saline. In some preferred forms, the sugar is a sugar alcohol, and is preferably selected from the group consisting glycol, glycerol, erythritol, arabitol, Xylitol, Ribitol, Mannitol, Sorbital, Isomalt, Maltitol, Lactitol, and combinations thereof. For some embodiments, the most preferred sugar alcohol is Mannitol. In some preferred forms, the "one or more alcohols" are selected from the group consisting of solvent alcohols, fatty alcohols, and combinations thereof. Solvent alcohols are preferably selected from the group consisting of ethyl, methyl, isopropyl, and combinations thereof. In at least one preferred embodiment, the solvent alcohol is ethyl alcohol. Fatty alcohols are preferably selected from the group consisting of cetyl, myristryl, lauryl, and combinations thereof. In some preferred forms of the invention, the fatty alcohols are myristryl and lauryl alcohol.

In another embodiment of the invention, the tissue is contacted with a surfactant in addition to the steps of conditioning the collagen in the decellularized tissue and biologically preparing the decellularized tissue noted above. In some preferred forms, the surfactant is a tenside, and in other preferred forms is Tween 20. In yet other preferred forms, the surfactant is selected from the group consisting of ionic compounds, cationic compounds, zwitterionic compounds, nonionic compounds, and combinations thereof. Preferably, the nonionic compound is selected from the group consisting of fatty acids, cocamides, poloxamers, alkyl polyglucoside, and combinations thereof.

In another embodiment of the invention, the tissue is contacted with a lubricant or a surfactant having lubricant properties in addition to the steps of conditioning the collagen in the decellularized tissue and biologically preparing the decellularized tissue noted above. This step can also be combined with the step of contacting the tissue with a surfactant. Preferably, the lubricant or surfactant having lubricant properties is selected from the group consisting of hyaluronan, oils, non-sulfated GAGs, fibronectin, chondroiton $SO_4$, heparin $SO_4$, keratin $SO_4$, proteoglycans, decorin, serglycin, syndeum, aggrecon, heparin, and combinations thereof. Of these, hyaluronan is preferred.

In another embodiment of the invention, the methods above can further include a structural strengthening step. In preferred forms, the structural strengthening step comprises the steps of: contacting the tissue with a collagen or elastin cross-linking agent; and contacting the tissue with saline and an anti-mineralization agent. This method can also include the step of contacting the tissue with $H_2O$. In preferred forms, the collagen or elastin cross-linking agent is selected from the group consisting of water-soluble cross-linking agents, glutaraldehyde type agents, photoactivated dyes, carbodiimides, diaminohexane, chromium, vegetable tannins, non-enzymatic glycosylation agents, steroid-like compounds, and combinations thereof. In some preferred embodiments the collagen or elastin cross-linking agent is a steroid-like compound. One preferred steroid-like compound is ginsenoside Rg1. In some preferred embodiments, the anti-mineralization agent is selected from the group consisting of alpha-amino oleic acid, ethanol, citric acid and combinations thereof. Of these, a preferred anti-mineralization agent is citric acid. Generally, the biological preparation step comprises a mixture having at least 7 components selected from the group consisting of traditional cell culture media, serum, insulin, growth promoters, myofibroblast phenotype maintenance agents, L-glutamine, buffer, heparin, steroid-like compounds, Chondroitin sulfate, ethyl pyruvate, ascorbic acid, ascorbate, collagen cross-linking agent, co-enzyme, and antibiotic agents. One preferred steroid-like compound is Ginsenoside Rg1. One preferred collagen cross-linking agent is citric acid. Preferably, the biological preparation step comprises protein insudation. In preferred forms, the traditional cell culture media is selected from the group consisting of DMEM+F12, MEM, Hank's solution, JCI99, RPMI 1600, and combinations thereof. Serum is preferably selected from the group consisting of serum specific to the donor species, serum specific to the recipient species, analogous serum from putative recipient, and combinations thereof. Preferred myofibroblast phenotype maintenance agents are preferably selected from the group consisting of TGF-β1, TGF-β2, TGF-β3, bFGF, FGF2, sphingosine, sphingosine-1-phosphate, and combinations thereof. Preferred buffers are selected from the group consisting of Zwitterionic Buffers, EDTA-Tris, trimentylglycine, glycine, BES, MES, Hepes buffer, and combinations thereof. Preferred collagen or elastin cross-linking agents are selected from the group consisting of water-soluble cross-linking agents, glutaraldehyde type agents, photoactivated dyes, carbodiimides, diaminohexane, chromium, vegetable tannins, non-enzymatic glycosylation agents, and combinations thereof. Preferred antibiotic agents are selected from the group consisting of amphoterian-B, vancomycin, gentamicin, and combinations thereof.

In another aspect of the present invention, a solution for the treatment of tissue is provided. This solution generally comprises ethyl alcohol, lauryl alcohol, myristyl alcohol, and hyaluronan high molecular weight (HMW) salt. In some preferred forms, this solution also includes TWEEN 20. In other preferred forms, this solution also includes glycerol.

In another aspect of the present invention, a solution for the treatment of tissue is provided. This solution generally comprises one or more solvent alcohols, one or more fatty alcohols, one or more lubricants, one or more ECM protein restoration agents, and combinations thereof. This solution has the effect of conditioning the collagen present in said tissue.

In another aspect of the present invention, a solution for the treatment of tissue is provided. This solution generally comprises a serum solution comprising serum, cell culture medium, insulin, and buffer; a growth factor solution comprising one or more growth factors and at least one myofibroblast phenotype maintenance agent; a nutrient solution to accelerate cell seeding comprising steroid-like compounds, a collagen cross-linking agent; and at least one antibiotic. In preferred forms, the serum solution comprises serum specific to the donor or recipient species, DMEM+F12, Insulin, BFGF, L-glutamine, Hepes buffer, and heparin. Preferred growth factor solutions comprise Gensenoside Rg1, FGF-2, Co-enzyme Q10, and TGF-B1. Preferred nutrient solutions comprise Chondroitin $SO_4$, Ethyl pyruvate, Sphenogosine-1-phosphate, Ascorbic acid-2-phosphate and Ascorbate. Preferred antibiotics include amphoterian-B, vancomycin, and Gentamicin, with a mixture of all three of these being especially preferred.

In some preferred methods of preparing a tissue for engineering applications, the tissue is treated with more than one of the solutions described above. Ultimately, the goal of the methods is to provide a biological scaffold for cell reseeding. Advantageously, when the methods and solutions of the present invention are used, tissues experience less calcification compared to those tissues not treated with the solutions of the present invention. The addition of citric acid, which acts as an anti-calcification agent aids in this advantageous property of the present invention.

After the methods and solutions of the present invention have been executed and used, the present invention further provides a method of reseeding a decellularized tissue. Generally, this method comprises the steps of a seeding phase; and a cell differentiation and migration phase. Generally, the seeding phase comprises placing a decellularized tissue into a bioreactor; adding mesenchymal stem cell proliferating media into said bioreactor; adding bone marrow from said decellularized tissue recipient; to said bioreactor and allowing said bioreactor to incubate the contents therein. In some preferred forms, the incubation time is from 4-6 days. In preferred forms, the bioreactor has or is coated with a compound, solution, or agent that provides a non-adherent surface. One preferred agent is agarose. In preferred forms, a hypoxic environment is created within said bioreactor. A preferred hypoxic environment is created by having an oxygen content from 3% to 19% within said bioreactor. Preferably, the oxygen content is about 7% in said bioreactor. Preferably, the methods further include the addition of nutrients to supplement the mesenchymal stem cell proliferating media.

The cell differentiation and migration phase generally comprises the following steps:

(a) Placing a decellularized tissue in a bioreactor with bone marrow cells;
(b) adding the serum solution noted above that comprises serum, cell culture medium, insulin, and buffer; a growth factor solution comprising one or more growth factors and at least one myofibroblast phenotype maintenance agent; a nutrient solution to accelerate cell seeding comprising steroid-like compounds, a collagen cross-linking agent; and at least one antibiotic;
(c) creating a hyperoxic environment within said bioreactor;
(d) introducing a mechanical environment; and
(e) allowing said decellularized tissue to incubate.

In preferred forms of this method, the bioreactor is prepared for the seeding phase, as described above, and for the cell proliferation phase, described below. In preferred forms, the hyperoxic environment comprises an oxygen content of about 22% to 70%, and is preferably about 50%. Generally, the mechanical environment comprises cyclic pressure and cyclic flow. Additionally, in preferred forms, the bone marrow cells differentiate into valve interstitial cells and valve endothelial cells. In some preferred forms, the method further comprises a cell proliferation phase. When such a step is included, the cell proliferation phase precedes the seeding phase and the cell differentiation and migration phase. Generally, the cell proliferation phase comprises the steps of harvesting bone marrow from a patient receiving a decellularized tissue; placing the harvested bone marrow into a bioreactor; adding mesenchymal stem cell proliferating media; and allowing the cells to incubate in the bioreactor. In preferred forms, a hypoxic environment is created within said bioreactor. Additionally, it is preferred that the bioreactor has non-adherent surfaces therein, or is coated with a non-adherent compound, solution, or agent. One preferred non-adherent agent is agarose. It is preferred that nutrients are added to supplement the mesenchymal stem cell proliferating media. Preferably, the hypoxic environment is created by having an oxygen content from 3% to 19%, more preferably between 4 and 15%, still more preferably between 5 and 11%, even more preferably between 6 and 8%, and most preferably about 7%, in the bioreactor. Using the method of the present invention, the said bone marrow amplifies and proliferates without differentiating. Additionally, anywhere from 1 to 3 bioreactors can be utilized in performing the steps of the invention.

DETAILED DESCRIPTION OF THE PREFERRED EMBODIMENTS

The following examples set forth preferred materials and procedures used in accordance with the present invention. It is to be understood, however, that these examples are provided by way of illustration only, and nothing therein shall be deemed to be a limitation upon the overall scope of the present invention.

EXAMPLE 1

This example illustrates one embodiment of the Collagen Conditioning Step—Phased ECM protein valve matrix preparation.

Materials and Methods

The process began using a decellularized heart valve. The tissue was then rinsed in sterile NS×3 A (200 cc/valve in hood—aseptic technique). The valve was then transferred into a sterile 250 cc wide mouth screw cap flask. The valve was then placed in Solution #5 consisting of 200 cc 2×NS+

Mannitol (18 gm/Nacl/SL 0.9% physiologic saline (NS)+25 gm Mannitol/2 L), in a sterile technique in hood, then rocked on a rocker plate for 1 hour at 21° C. and 25 RPM. The valve and solution were then decanted and covered with 200 to 250 cc of a second collagen conditioning solution, Solution #2. It was then rocked gently at 30 RPM at 37° C.×30 minutes Solution #2 was made by combining a first solution, "Solution A" with a second solution, "Solution B." Solution A was made in a container by adding:
- 2.42 gm Cetyl alcohol $CH_3(CH_2)_{15}OH$ (2.42 gm/mole) 0.005 (a/k/a) Palmityl alcohol
- 100 cc Ethyl alcohol (EtOH—100%/200 proof)
- 1.86 gm Lauryl alcohol $C_{12}H_{26}O$ (186.34 gm/mole) Soluble ETOH
- 2.1 gm Myristyl alcohol (214.39 gm/mole) Soluble ETOH
- 80 μgm Hyaluronan ($HAK^+$ salt) HMW salt 0.8 μgm/ml
- Normal Saline 0.9% $NaCl/dd\ H_2O$ In a second container, the following ingredients were added to form "Solution B":
- 10 mgm Heparin (Sodium salt 170 USP units/mgm—Sigma Aldrich)
- 0.01% V/V Tween 20
- Glycerol 0.2 cc (0.01% V/V)
- 120 cc "Degassed" normal saline Solution B was then slowly added to solution A on a warming/rocker plate at 37° C. If any additional fluid was needed to cover the valve, 5% Albumin/FBS, plasma, or species-specific serum, and combinations thereof, was used. The valve was then covered with the combination of solutions A and B (about 200 cc) and then rocked gently for 30 minutes at 37° C.

The solution and valve were then decanted and washed with NS×1 in a hood under sterile conditions for 4 hours. The valve was then stored in the "post decell storage solution" at 4° C. for up to five days.

The post decell storage solution included the following:
- 470 ml Lactated Ringers
- 4× Amphotericin B (20 ml/250 ml)
- 2× Pen/Strep 10 ml/250 ml
- Cipro (stock: 10 mg/ml suspension) used 2 mg/250 ml=0.2 ml/250 ml
- Vancomycin (2.5 ug/ml stock) at 1 ml/500 ml
- 12.5 gm Mannitol (aq)

EXAMPLE 2

This example illustrates a preferred structural Protein Strengthening Step.
Materials and Methods The valve was removed from storage in the post decell solution and rinsed in sterile NS×3(200 cc per valve in hood—aseptic technique) at 21° C. before being transferred into an individual container with Solution # 3 which included 250 cc $ddH_2O$+Ginsenoside Rg1 (AHP ChromaDex™, Santa Ana, Calif. 98% purity) 50 ngms/ml×2 hours on rocker plate at a pH of 7.4 and a temperature of 21° C. [50 ngms/ml×250 ml=12.5 μgms/valve]. The valve was then rinsed three times in PBS and was placed in #4 by carefully adding 2 L of normal saline solution to 200 ml of a 1N citric acid solution. The valve was then covered with the 0.1 N citric acid solution and placed on a gentle rocker plate for 15 minutes at 30 RPM in a hood using sterile technique. The valve was then removed and rinsed three times in PBS and then stored at 4° C. in freshly made Post-Decell storage solution, as described in Example 1.

EXAMPLE 3

This example illustrates the biological preparation step before cellular reseeding.
Materials and Methods The valve was removed from the post decell storage solution from Example 1 and washed twice in NS for 15 minutes for each wash on a gentle rocker plate at 21° C. The valve was then placed in mesenchymal stem cell proliferating media (non-differentiating) (Lonza Group Ltd, Switzerland) in a bioreactor (500 cc) covering the valve. Seeding into the valve tubular space (leaflet) began at 37° C., 5% $CO_2$, 19% $O_2$ for 24 hours. The valve was then placed in the post decell storage solution of Example 1 solution #1, which is used in this context as a pre-op seeding solution.

Prior to surgery start time using sterile technique including mask, gown, gloves, and hood, the valve was rinsed in sterile dd $H_2O$+30% ETOH (by volume—200 proof) and then placed on a rocker plate for 15 minutes at 15 RPM. The valve was then rinsed two times in sterile normal saline ("NS"). Next, the valve was placed in solution #1, being used as a smart seeding solution. This embodiment of solution 1 was made by admixing the following in a 500 cc volume bioreactor:

Media
- Serum specific to the donor species or recipient species—200/cc per valve
- DMEM+F12=300 cc/valve
- Insulin 2 units/ml (100 units/500 ml)
- BFGF 2 nmg/ml (Sigma)
- L Glutamine (0.03%) 2 mM
- Hepes buffer (15 mM)
- 1000 units Heparin/500 cc bioreactor volume (2 u/cc)

Special growth factors to differentiate myofibroblasts were also added to the solution. These growth factors were:
- Ginsenoside Rg1 (ChromaDex™, Santa Ana, Calif.=98% purity) 10 ngm/ml
- FGF-2 10 ng/ml (Sigma)
- Co-Enzyme Q10:1.4 μgm/ml
- TGF-B1: 20.09 ngm/ml (5050—Sigma: prepare as 10× stock 5 ml aliquots—freeze (20° C.—thaw on day of use to preserve bioactivity) 20 nmg/ml×500 ul Special nutrients to accelerate seeding were also added. These nutrients included:
- Chondroitin $SO_4$ 20.0 μgm/ml (Sigma)
- Ethyl Pyruvate: 30 mM
- Sphingosine-1-phosphate: 100 ngm/valve/500 cc vial=0.2 ngm/ml
- Ascorbic Acid—2 phosphate 200 μgm/ml in 500 ml (A 8960 Sigma)=40 μgm/ml
- Ascorbate=50 μgm/ml Antibiotics used were:
- Amphoterian-B 25 μgm/ml
- Vancomycin 50 μgm/ml
- Gentamicin 500 μgm/ml All proteins used were recombinant preparations or human analogs.

EXAMPLE 4

This example illustrates an alternate embodiment of the collagen conditioning methodology described in Example 1.
Materials and Methods This method began using a decellularized heart valve. If the valve was cryopreserved, the valve was thawed and storage solutions removed according to the guidelines received from the entity used for cryopreservation. The valve (whether stored in the post decell storage solution or not) was rinsed in sterile NS×3 A (200 cc/valve in hood—aseptic technique) before being transferred into a sterile 250 cc wide mouth screw cap flask. The valve was then placed in 200 cc 2×NS+mannitol ((18 gm/Nacl/SL 0.9% physiologic saline (NS)+25 gm Mannitol/2 L)), sterile technique in hood, then on a rocker for 1 hour, 21° C., 25 RPM. The valve was then decanted and covered with 200 to 250 cc of Solution 2 (as provided below) to condition the collagen and rocked gently at 30 RPM at 39° C.×5 minutes as below.
(Alternate Solution #2)
Soln.-A 200 cc Ethyl alcohol (EtOH—100%/200 proof)
 4.65 cc Lauryl alcohol $C_{12}H_{26}O$ (186.34 gm/mole)
 4.2 gm Myristyl alcohol (214.39 gm/mole)
 160 μgm Hyaluronan (HAK$^+$ salt) HMW salt
Soln.-B
 240 cc "Degassed" normal saline
 [0.01% V/V Tween 20]—omit—optional
 [Glycerol 0.2 cc (0.01% V/V]—omit—optional
 Solution B was brought to 45° C. and Solution A was brought to 40° C. before adding Solution B to Solution A slowly on a warming/rocker plate at 40° C. until the beginning of any precipitate formation, or once achieving 40% ETOH/$H_2O$ V/V. The resultant solution (Solution 2) was then sterile filtered and before adding the valve, was cooled at 39° C. and combined with 1700 units sterile heparin. (10 mgm Heparin (Sodium salt 170 USP units/mgm—Sigma Aldrich). The valve was covered with this resultant solution (≈400 cc) and gently rocked for 5 minutes at 39° C. Solution 2 was then decanted from the valve and the valve was rinsed one time in post decell storage solution (from Example 1) (hood-sterile conditions) and placed on a gentle rocker plate at 21° C. for 30 minutes. The valve can then be stored in the post decell storage solution at 4° C.

EXAMPLE 5

This example illustrates an alternate structural protein strengthening step.
Materials and Methods The valve was removed from storage. If the valve was not stored at 4° C. in the post-decell storage solution described in Example 1, all of the storage solutions were rinsed and diluted per their preferred protocol. If the valve was stored at 4° C. in the post decell storage solution of Example 1, the valve was rinsed in sterile NS three times (200 cc/valve in hood—aseptic technique) before being transferred into Solution 3 comprising individual 200 cc dd$H_2$O+Ginsenoside Rg1 (AHP ChromaDex™, Santa Ana, Calif. 98% purity) 50 ngms/ml for 2 hours on a rocker plate at a pH of 7.40 and a temperature of 21° C. 50 ngms/ml of gensenoside Rg1 were used in 200 cc of solution. 200 cc of solution were used for one valve. The valve was then rinsed in NS and decanted before being covered with Solution 4 comprising 200 ml of a 1N citric acid solution in 2 L of normal saline solution. The valve was then gently rocked on a rocker plate for 15 minutes at 30 RPM (hood) before being rinsed one time with NS. The valve can then be immediately pretreated for enhanced seeding or recellularizing or it can be stored at 4° C. in the freshly made post-decell storage solution from Example 1.

EXAMPLE 6

This example illustrates an alternative methodology for the biological preparation step before cellular reseeding. This pretreatment accelerates myofibroblasts and endothelial cells cellular in vivo in migration and/or in vitro cell seeding.
Materials and Methods If the valve is not already in NS or in the post decell storage solution from Example 1, the valve was washed in NS one time for 15 minutes on a gentle rocker plate at 21° C. Otherwise, the valve was then placed in 250-500 cc recipient plasma (ideal) (or fresh frozen species specific—e.g. human, plasma)+antibiotics for 24 hours in a wide mouth screwtop tissue jar at 4° C. Preferred antibiotics include Amphotericin B 25 μgm/ml, Vancomycin 50 μgm/ml, Gentamicin 500 μgm/ml, and combinations thereof. The plasma was then augmented with 5% Plasma-Lyte or fresh frozen species specific (human) plasma as necessary for volume to cover the valve. The valve was then moved in a sterile hood to a seeding bioreactor and secured using fixation adaptors.

EXAMPLE 7

This example provides a three-day bioreactor seeding method for tissue engineered heart valves in accordance with the present invention.
Materials and Methods Decellularized valves that had undergone the three-step regimen of the present invention, were stabilized in fresh mesenchymal stromal cell proliferation media [e.g. Lonza #PT-3001, MSCGM™ BulletKit® and PT-3238, MSCBM] for 3 hours at 37° C. at 20% $O_2$ triflow settings, while cells were obtained from the potential heart valve recipient. On day one, the valve was moved to a sterile 250 cc spinner flask with air filters attached and mesenchymal stromal cell proliferating media (nondifferentiating) was added in a bioreactor (500 cc) to cover the valve. All available bone marrow "BM" cells were then seeded into valve tubular space (supraleaflet) and static seeding proceeded at 37° C., 5% $CO_2$, 20% $O_2$ for 24 hours, [e.g., "Marrow Max"© Bone Marrow, (Invitrogen, Cat #12260-014), or Mesencult© Media, Blood Medium for human mesenchymal stem cells (Stem Cell Technologies, #5401) or Lonza #PT-3001, MSCGM™ BulletKit® and PT-3238, MSCBM]. The blood medium or Lonza #PT-3001 were nutrient blends to use with the media as a supplement. Fetal bovine serum or 10 cc recipient serum was then added. The tissue engineered heart valve was then seeded with 20 cc filtered bone marrow containing 1000 U Heparin per 20 cc/syringe. Pulsatility was started at 60 BPM, with a pressure wave at 20/5 mm Hg. This pressure was ramped at 3 to 6 hour intervals×2 to 120/40 mm Hg creating cyclic pressure and cyclic flow. The cell suspensions for preseeding were prepared by taking 8-20 cc or more bone marrow from the recipient patient and aspirating via direct coarse syringe filter to remove bone particles, but not cells, and then transferred to the bioreactor flask. Alternatively, mesenchymal stem cells can be obtained by placing the bone marrow into a growth chamber and creating cyclic flow such that the mesenchymal stem cells adhere to the outside of the growth chamber. Those mesenchymal stem cells can be harvested and utilized. This is a separation step which takes raw bone marrow and locates the mesenchymal stem cells. $1 \times 10^6$ of each cell type and 8 cc bone marrow were aspirated.

On Day 2, proliferation media was discarded and replaced with Solution 1 @37° C. in asterile pulsatile bioreactor for 24 hours with 5% $CO_2$, 50% $O_2$, 45% $N_2$. The pH was monitored. The ideal pH is from 6.4 to 7.4. A falling pH indicates active metabolism and that the cells are proliferating.

High cyclic pressure was used here to condition the heart valve for implantation. Solution 1 (cell culture solution) contains components that have advantages. The hyperoxia at these levels enhances myofibroblast (the primary valve interstitial cell—VIC) proliferation and migration. The pulsitility was started at a physiologic heart rate of 60 beats per minute and the pressure wave forms were tuned initially to right sided or pulmonary artery pressures and then are ramped up at three to six hour intervals to systemic pressures of 120 over 40 mm Hg. The lower diastolic was designed to increase the pulse pressure width which is perceived by the cells as a greater dp/dt and thus a greater load and load differential which enhances acclimization to a functioning VIC phenotype. Systemic pressures were used even for right sided valve conduits as the goal was to achieve the strongest valve structural protein-cell combination and thus stimulating the synthesis of structural proteins and adaptation increased cellular wall tension, increased cell density and added to the maintenance of cell phenotype for a stronger and more rapidly adapting tissue engineered heart valve after transplantation into the patient.

Solution 1 was prepared fresh each day of use at a pH of 7.40

Solution 1 was made by adding the following components into a 500 cc volume pulsatile bioreactor:
  Species specific serum or recipient specific serum=200 cc/valve (human, ovine or baboon)
  DMEM+F12=300 cc/valve
  Insulin 2 ngm/ml
  L Glutamine (0.03%) 2 mM
  Hepes buffer (15 mM)
  1000 units Heparin/500 cc bioreactor volume (2 u/cc)
  Special growth factors to differentiate myofibroblasts in this solution included:
  IGF 2 ngm/ml (Sigma)
  FGF-2 10 ng/ml (Sigma)
  TGF-β1: 20.0 ngm/ml (5050—Sigma: prepare as 10× stock 5 ml aliquots—
    freeze (20° C.—thaw on day of use to preserve bioactivity)
  Co-Enzyme Q10:1.4 μgm/ml
  Special nutrients to accelerate seeding in this solution included:
  Chondroitin $SO_4$ 20.0 μgm/ml (Sigma)
  Ethyl Pyruvate: 30 mM [3.48 gms/l; 3.33 cc/l; 1.67 cc/500 cc of stock 1.045 g/ml density]
  Sphingosine-1-phosphate: 100 ngm/valve/500 cc vial=0.2 ngm/ml
  Ascorbic Acid—2 phosphate 200 μgm/ml in 500 ml (A 8960 Sigma)=40 μgm/ml
  Ascorbate: 50 μgm/ml
  Antibiotics included in this solution included:
  Amphoterian-B 25 μgm/ml
  Vancomycin 50 μgm/ml
  Gentamicin 500 μgm/ml
  All proteins are recombinant preparations; or human analogues.

On Day 3, the scaffold was seeded in vitro in a pulsatile bioreactor such that the cells could differentiate. Half of the solution currently in the bioreactor was replaced with fresh pre-warmed Solution 1 covering the valve in bioreactor. 120/40 mmHG pulsations were resumed in the pulsatile bioreactor. The valve was placed in a Triflow incubator with the settings of 37° C. incubator, 5% $CO_2$ 32 torr, 50% $O_2$ 380 torr, and 45% $N_2$ 348 torr.

The bioreactor held 750 cc total volume and 250 cc of plasma were used, making up 33% of the volume of the bioreactor. The bioreactor was capable of producing pressures and flexibility similar to those experienced under physiological conditions.

Days 4-6 involved in vitro preseeding, where the cells continue to differentiate. Half of the solution the valve was in was replaced with fresh Solution 1 (as described above). The valve was then pulsed at 37° C. in a triflow incubator for 18 to 24 hours (or longer prn OR start time) at a maximum of 60 BPM at 120/40 mm Hg ventricular outflow or sinewave waveforms. The day the valve is implanted, again, half of the solution was replaced with fresh Solution 1. Dextran $SO_4$ negatively charged (DxS 5 kda, pK decimals A./S, Koge, Denmark) was added to the bioreactor with the valve. 5 μgm/ml Dexatran sulfate was added to the bioreactor for extracellular volume compression (EVC). The bioreactor was then resumed at 60 BPM ($1H_z$) at 120/40 mm Hg until ready to implant.

The valve is ideally implanted the same day as the above protocol. The valve was implanted within 72 hours of seeding. For implantation, the valve was removed from the bioreactor and placed in heparinized oxygenated recipient blood or on a table into it is ready to sew into position. Ideally, the valve only sits in the blood for 5 to 25 minutes. Placing the valve in recipient blood helped to prevent cell shock when the valve was implanted.

EXAMPLE 8

This example illustrates one embodiment of the preparation of Solution 5.

Materials and Methods
  The following were combined in a sterile container:
  200 cc 2×NS
  mannitol (18 gm/NaCl/SL 0.9% physiologic saline (NS)+ 25 gm Mannitol/2 L) 1.8 g NaCl
  Harvested tissue was placed in a sterile container. The solution was then added to the container and allowed to rock on a rocker plate for 1 hour at 21° C. at 25 RPM.

EXAMPLE 9

This example illustrates one embodiment of how to prepare Solution #2.

Materials and Methods
  In a first container, the following ingredients were added to form "Solution A":
  200 cc Ethyl alcohol (EtOH—100%/200 proof)
  4.65 cc Lauryl alcohol $C_{12}H_{26}O$ (186.34 gm/mole) Soluble ETOH
  4.2 gm Myristyl alcohol (214.39 gm/mole) Soluble ETOH
  160 μgm Hyaluronan (HAK$^+$ salt) HMW salt
  In a second container, the following ingredients were added to form "Solution B":
  240 cc "degassed" normal saline
  [0.01% V/V Tween 20]—optional
  [Glycerol 0.2 cc (0.01% V/V)]—optional Solution B was brought to 45° C. and Solution A was brought to 40° C. Solution B was then slowly added to Solution A on a warmer/rocking plate at 40° C. The rocker plate was stopped when precipitate began to form or once the solution reached 40% ETOH/H$_2$O V/V. The solution was then filtered using a sterile filter, and allowed to cool to a temperature of 39° C. At this point the valve was placed in the solution and 1700 units of sterile heparin were added (10 mgm Heparin (Sodium salt 170 USP units/mgm—Sigma Aldrich). Once the valve was covered in the solution it was allowed to gently rock for 5 minutes at 39° C.

EXAMPLE 10

This example illustrates one embodiment of the preparation of Solution 3.
Materials and Methods
The following were admixed in a sterile container:
250 cc ddH$_2$O
50 ngms/ml Ginsenoside Rg1 (AHP ChromaDex™ 98% purity (Santa Ana, Calif.))
The solution was then placed on a rocker plate for 2 hours at 21° C. The pH of the solution was 7.40.

EXAMPLE 11

This illustrates one embodiment of how to prepare Solution 4.
Materials and Methods
200 ml of a 1N citric acid was carefully added to 2 L normal saline solution. This solution was poured over harvested tissue and covered. The tissue and solution were then allowed to rock on a rocking plate for 15 minutes at 30 RPM.

EXAMPLE 12

This example illustrates one method of making one embodiment of Solution 1.
Materials and Methods
This solution was made at a pH of about 7.40. The container used was a 500 cc volume bioreactor. The following were added to the bioreactor:
1. Media:
   DMEM+F12=300 cc/valve
   Serum specific to the donor species or recipient species—200/cc per valve
   Insulin 2 units/ml (100 units/500 ml)
   Hepes buffer (15 mM)
   1000 units Heparin/500 cc bioreactor volume (2 u/cc)
2. Special Growth Factors to Differentiate Myofibroblasts:
   IGF 2 ngm/ml (Sigma)
   FGF-2 10 ng/ml (Sigma)
   TGF-B1: 20.0 ngm/ml (5050—Sigma: prepare as 10× stock 5 ml aliquots—freeze (20° C.—thaw on day of use to preserve bioactivity)
   Co-Enzyme Q10:1.4 μgm/ml
3. Special Nutrients to Accelerate Seeding:
   Chondroitin SO$_4$ 20.0 μgm/ml (Sigma)
   Ethyl Pyruvate: 30 mM [3.48 gms/l; 3.33 cc/l; 1.67 cc/500 cc of stock 1.045 g/ml density]
   Sphingosine-1-phosphate: 100 ngm/valve/500 cc vial=0.2 ngm/ml
   Ascorbic Acid—2 phosphate 200 μgm/ml in 500 ml (A 8960 Sigma)=40 μgm/ml
   Ascorbate=50 μgm/ml
4. Antibiotics:
   Amphoterian-B 25 μgm/ml
   Vancomycin 50 μgm/ml
   Gentamicin 500 μgm/ml
   All proteins used were recombinant preparations or human analogs.

EXAMPLE 13

This example illustrates an alternate embodiment for making Solution #2.
Materials and Methods
In a first container, the following ingredients were added to form "Solution A":
2.42 gm Cetyl alcohol CH$_3$ (CH$_2$)$_{15}$OH (2.42 gm/mole) 0.005 (a/k/a) Palmityl alcohol
100 cc Ethyl alcohol (EtOH—100%/200 proof)
1.86 gm Lauryl alcohol C$_{12}$H$_{26}$O (186.34 gm/mole) Soluble ETOH
2.1 gm Myristyl alcohol (214.39 gm/mole) Soluble ETOH
80 μgm Hyaluronan (HAK$^+$ salt) 0.8 μgm/ml dissolve in 100 cc ddH$_2$O/NS
In a second container, the following ingredients were added to form "Solution B":
10 mgm Heparin (Sodium salt 170 USP units/mgm—Sigma Aldrich)
0.01% V/V Tween 20
Glycerol 0.2 cc (0.01% V/V)
120 cc "degassed" normal saline
Solution B was then added to Solution A slowly on warming/rocker plate at 37° C. which made about 200 cc of solution. The valve was then covered with the mixture of A and B on the warming/rocker plate and allowed to rock gently for 30 minutes at 37° C.
5% Albumin/FBS, plasma, or serum specific to the species of the intended engineered tissue recipient was used as additional fluid to cover the engineered tissue.

EXAMPLE 14

This example illustrates an alternate embodiment of making Solution 1.
Materials and Methods
The container used was a 500 cc volume bioreactor. The following were added to the bioreactor:
1. Media:
   Serum specific to the donor species or recipient species—200/cc per valve
   DMEM+F12=300 cc/valve
   Insulin 2 units/ml (100 units/500 ml)
   BFGF 2 nmg/ml (Sigma)
   L Glutamine (0.03%) 2 mM
   Hepes buffer (15 mM)
   1000 units Heparin/500 cc bioreactor volume (2 u/cc)
2. Special Growth Factors to Differentiate Myofibroblasts:
   Ginsenoside Rg1 (ChromaDex™, Santa Ana, Calif.=98% purity) 10 ngm/ml
   FGF-2 10 ng/ml (Sigma)
   Co-Enzyme Q10:1.4 μgm/ml
   TGF-B1: 20.09 ngm/ml (5050—Sigma: prepare as 10× stock 5 ml aliquots—freeze (20° C.—thaw on day of use to preserve bioactivity) 20 nmg/ml×500 u 3. Special Nutrients to Accelerate Seeding:
   Chondroitin $SO_4$ 20.0 μgm/ml (Sigma)
   Ethyl Pyruvate: 30 mM
   Sphingosine-1-phosphate: 100 ngm/valve/500 cc vial=0.2 ngm/ml
   Ascorbic Acid—2 phosphate 200 μgm/ml in 500 ml (A 8960 Sigma)=40 μgm/ml
   Ascorbate=50 μgm/ml
4. Antibiotics:
   Amphoterian-B 25 μgm/ml
   Vancomycin 50 μgm/ml
   Gentamicin 500 μgm/ml
*All proteins used were recombinant preparations or human analogs.

EXAMPLE 15

This example provides an alternate embodiment of the collagen conditioning solution, method of making, and method of use.
Materials and Methods
Collagen Conditioning A heart valve was stored in post decell storage solution, as in Example 1. Alternatively, the valve was cryopreserved, and in this alternate embodiment, the valve was brought to room temperature before the next step.

Next, the valve was rinsed, diluted, and all storage solutions were removed. The valve was then rinsed in sterile NS×3 A (200 cc/valve in hood—aseptic technique) and transfered into a sterile 250 cc wide mouth screw cap glass jar.

The valve was then placed in 200 cc 2×NS+Mannitol ((18 gm/NaCl/SL 0.9% physiologic saline (NS)+25 gm Mannitol/2 L)), using sterile technique in hood, then placed on a rocker plate for 1 hour, 21° C., at 25 RPM. The valve was then rinsed in Solution 2, according to the present invention. The valve was then allowed to decant in 200 to 250 cc of Solution 2, while rocking gently at 30 RPM at 39° C.×5-7 minutes. Solution 2 was made by the following method:

Solution 2 was made by admixing solution A and solution B as described below:
Soln.-A: The following were mixed in a sterile container:
   200 cc Ethyl alcohol (EtOH—100%/200 proof)
   4.65 cc Lauryl alcohol $C_{12}H_{26}O$ (186.34 gm/mole)
   4.2 gm Myristyl alcohol (214.39 gm/mole)
Soln.-B: The following were mixed in a sterile container:
   "Degassed" sterile filtered 240 cc normal saline
   160 μgm Hyaluronan (HAK$^+$ salt) HMW salt
   1.54 gm citric acid [Sigma #C2404-500G]
   [0.01% V/V Tween 20]—omit—optional Solution B was brought to a boil at 45° C. and solution A was brought to 40° C. Then, Solution B was added to solution A slowly on warming/rocker plate at 40° C. The rocking was stopped at the beginning of any precipitate formation, or once 40% ETOH/$H_2O$ V/V was achieved. A Sterile filter was used, then before covering the valve with solutions A and B, the valve was cooled to 39° C. The valve was then covered with A+B (≈400 cc) and gently rocked for 5-7 minutes at 39° C. The valve was then allowed to decant in the solution. A rinse in post decell storage solution, as in Example 1, was performed 1 time (hood-sterile conditions) and then gently rocked for 30 minutes at 21° C. 1700 units sterile heparin was then added. (10 mgm Heparin (Sodium salt 170 USP units/mgm—Sigma Aldrich). Afterwards, the treated valve was stored in the post decell solution, according to Example 1, at 4° C.

Results and Conclusions

The collagen conditioning solution (Solution 2) includes a number of alcohols which restore collagen triple helix conformation and the collagen-to-collagen fibril alignment. The Heparin restored molecular polarity and the Hyaluronan re-established a moisture envelope around the collagen and elastin fibers that is similar to the normal GAG functionality. When used, the Tween 20 functioned as a surfactant and humectant.

The process of washing and removing all cells and cellular material leaves voids in the structure of the wall and the leaflets. These voids collapse upon "loading" of the valve when placed in a functioning hemodynamically functioning position. Since the valve interstitial cells have contractile functionality and provide additional tension during deformation, some of the visco elastic properties are slightly altered during decellularization. Thus, this step provided a safety margin of passive material strength. Citric acid demonstrated such an effect and also restores the proper pH that prepares the graft for the biological treatment. Citric Acid is also an anticalcification treatment.

At the conclusion of decellularization, there is an element of collagen "fraying" as well as loss of collagen alignment. Therefore, these steps initially wash out the storage solution and the hypertonic solution withdraws some of the water from the tissues, creating an osmotic pump to enhance ingress of Solution 2.

EXAMPLE 16

This example provides for an alternate embodiment of the biological preparation step, specifically, protein insudation.
Materials and Methods
Biological Preparation.

The valve was pretreated to accelerate BM-MSC, MYFB and EC cellular in vivo adhesion, in-migration and/or in vitro cell seeding. The valve was then washed in sterile normal saline and 10 mgm (10,000 units) Heparin for 15 minutes on gentle rocker plate at 21° C. The valve was then placed in 250-500 cc recipient plasma (ideal) (or fresh frozen species specific—e.g. human, plasma) or 5% hAlbumin and antibiotics for 24 to 72 hours at 4° C. The antibiotics used were the following:
   Amphotericin B 25 μgm/ml
   Vancomycin 50 μgm/ml
   Gentamicin 500 μgm/ml The antibiotics may be augmented with 5% Plasma-Lyte or fresh frozen species specific (human) and extra plasma as necessary for volume to cover valve. A bioreactor was used for the valve and the solution.

EXAMPLE 17

This example illustrates the reseeding process incorporating Solution 1.
Materials and Methods The reseeding process involves three phases: the Proliferation Phase, the Seeding Phase, and the Differentiation and Migration Phase. In the Proliferation Phase, 1 gm Ancef into the bone marrow donor 1 hour before bone marrow harvest. Bone marrow was harvested from the heart valve recipient. The decellularized and conditioned (according to the methods of the present invention) is attached in a bioreactor and set aside. A separate incubator is set up for the bone marrow. The incubator for the bone marrow is a bioreactor which was set to an equilibrium of 20% $O_2$, 5% $CO_2$, for 1-2 hours prior to adding the bone marrow. The incubator was set to 0.25 mm/second. Additionally, the incubator was coated with agarose so that the bone marrow cells do not adhere to the wall of the incubator creating spheroid bodies of mesenchymal stromal cells. Then, 500 mL of fresh sterile complete mesenchymal stem cell proliferating media (MSCGM) media (Lonza Group Ltd., Switzerland). The incubator was set to 37° C. Using a syringe, unfiltered heparinized bone marrow (1000 units of heparin/25 mL bone marrow) was placed into the incubator. The bone marrow was incubated at an oxygen content of 3-19%, with 7% being optimal. The bone marrow cells were left to incubate for 48-96 hours. This Proliferation Phase allows the proliferation of bone marrow cells while preventing differentiation of those cells.

In the next phase, the Seeding Phase, the valve was added to the incubator with fresh MGCSM and MCGM (nutrient pellet to supplement the MGCSM media). The mesenchymal component of the bone marrow was seeded into the scaffold of the valve as a result of this process. The incubator at this stage was considered a hypoxic incubation since the oxygen content was around 7%. This hypoxic environment helped prevent bone marrow differentiation. The valve was allowed to incubate for 4-7 days. The pH of the solution is optimally about 6.4 to 7.2. A falling pH is an indicator that the cells are proliferating, but the pH should be kept above 6.2. It was during this phase that the mesenchymal stem cells adhere to the valve.

In the third phase, or the Differentiation and Migration Phase, the MSCGM media is discarded and replaced with Solution 1 in the bioreactor containing the heart valve and bone marrow. Prior to the addition of Solution 1, the oxygen environment was altered such that it became a hyperoxic environment, having 22% to 70% oxygen, with 50% being optimal. Solution 1 was prepared as directed below:
The following were admixed in a sterile container:
Species specific serum or recipient specific serum (20%; 100 mL/valve)
DMEM+F12 (250 mL/valve)
Insulin 2 ng/ml
L Glutamine (0.03%) 2 mM
Hepes buffer (15 mM)
1000 units Heparin/500 mL bioreactor volume (2 U/mL)
IGF (2 ng/ml)
FGF-2 (2 ng/ml)
TGF-β1 (1.0 ng/ml)
Co-Enzyme Q10 (1.4 µg/ml)
Chondroitin SO4 (20.0 µg/ml)
Ethyl Pyruvate (30 mM)
Sphingosine-1-phosphate (0.2 ng/ml)
Ascorbic Acid—2 phosphate (40 µg/ml)
Ascorbate (50 µg/ml)
Amphotericin-B (1 µg/ml)
Vancomycin (25 µg/ml)
Gentamicin (50 µg/ml)
Dextran $SO_4$ (5 µgm/mL)

The addition of Solution 1 allowed the mesenchymal stem cells to begin to differentiate and migrate further into the scaffold of the valve. This process allowed for differentiation, proliferation, and migration for valve interstitial and valve endothelial cells, thus, repopulating the valve. Next, a mechanical environment was introduced into the bioreactor such that cyclic pressure and cyclic flow was occurring. This process conditioned the valve to the flow in the heart so that it had a better chance of success once implanted. Half of Solution 1 was replaced when the pH of the bioreactor environment fell to less than 6.4. Since a 500 cc bioreactor was used, 250 cc of fresh Solution 1 was replaced in the bioreactor when the pH fell to less than 6.4 or every 36 hours. This process was repeated over the course of 3-5 days. Cyclic rates for the bioreactor started at 3 mmHg/0 (10-20 beats per minute) and was ramped up gradually each day to a final cyclic pressure of 25 mmHg/10 (20-100 beats per minute).

Results and Conclusions

Valves were conditioned and mesenchymal stem cells were seeded into the valve, proliferated, differentiated, and migrated throughout the valve.

I claim:

1. A composition comprising decellularized tissue suspended in a solution comprising:
   i) −20 % to 60 % of ethyl alcohol;
   ii) 0.03 to 0.75 M of lauryl alcohol;
   iii) 0.03 to 0.75 M of myristyl alcohol; and
   iv) 30 to 300 µg/L of hyaluronan high molecular weight (HMW) salt.

2. The solution of claim 1, further comprising citric acid and/or heparain.

3. The solution of claim 1, further comprising glycerol.

4. A solution for the treatment of decellularized tissue consisting essentially of:
   i) 20 % to 60 % of ethyl alcohol;
   ii) 0.03 to 0.75 M of lauryl alcohol;
   iii) 0.03 to 0.75 M of myristyl alcohol;
   iv) 30 to 300 µg/L of hyaluronan HMW salt;
   v) about 1 to 9 g/L of citric acid;
   vi) normal saline; and
   vii) heparin.

5. The method according to claim 1, further comprising normal saline.

* * * * *